(12) United States Patent
Wilk

(10) Patent No.: US 6,780,439 B2
(45) Date of Patent: Aug. 24, 2004

(54) WOUND TREATMENT SOLUTION AND METHOD FOR USING SAME

(76) Inventor: J. Ronald Wilk, 608 Water Oak Dr., Plano, TX (US) 75025

( * ) Notice: Subject to any disclaimer, the term of this patent is extended or adjusted under 35 U.S.C. 154(b) by 0 days.

(21) Appl. No.: 09/800,360

(22) Filed: Mar. 6, 2001

(65) Prior Publication Data

US 2003/0158165 A1 Aug. 21, 2003

(51) Int. Cl.⁷ ............................. A61K 9/08; A61K 33/30
(52) U.S. Cl. ....................... 424/642; 424/400; 424/401; 424/641
(58) Field of Search ................................ 424/400, 407, 424/641, 642; 514/182

(56) References Cited

U.S. PATENT DOCUMENTS

| 5,266,318 A | | 11/1993 | Taylor-McCord | |
| 5,869,062 A | * | 2/1999 | Oliver | 424/195.1 |
| 5,879,717 A | | 3/1999 | McConn-Stern et al. | |
| 5,980,875 A | | 11/1999 | Mousa | |
| 6,099,866 A | | 8/2000 | Slimak | |
| 6,221,403 B1 | * | 4/2001 | Nesbit | 424/642 |
| 6,287,583 B1 | * | 9/2001 | Warren et al. | 424/404 |

* cited by examiner

Primary Examiner—Barbara P. Badio
(74) Attorney, Agent, or Firm—Jackson Walker L.L.P.

(57) ABSTRACT

A novel solution for the treatment of skin sores and wounds, consisting of cedar leaf oil, zinc oxide ointment, calamine lotion and an ointment base, is disclosed. The solution is prepared by combining the components in varying quantities, and may be applied to a sore or wound to promote healing and reduce scarring.

41 Claims, No Drawings

WOUND TREATMENT SOLUTION AND METHOD FOR USING SAME

BACKGROUND OF INVENTION

1. Field of Invention

The present invention relates generally to solutions for the treatment of sores, wounds, and other traumatized dermal tissues. The present invention relates more specifically to a solution comprised of cedar leaf oil, zinc oxide ointment, calamine lotion and an ointment base for the topical treatment of open wounds and ulcers of the skin.

2. Description of the Prior Art

The skin, mucus membranes and other dermal tissues of mammals, especially humans, is known to be susceptible to injury and infection. Human skin is especially prone to developing various sores or becoming otherwise traumatized due to injury, disease, exposure to toxins or caustic substances, and the like. Large wounds or sores covering relatively large surface areas of the skin such as burns, lacerations and diabetic ulcers, to name only a few, are often difficult to treat and may heal slowly. Some sores, especially diabetic skin ulcers, may not heal on their own, and can cause great distress to the patient suffering therefrom. If left untreated, a skin sore may become infected, and even gangrenous and may even lead to disfiguring scars or even to the loss of a limb.

For centuries, people have been using various substances, both naturally occurring and synthetic, in an effort to promote healing of skin tissues. Often, it is desirable that these substances be applied directly to the area of the wound or sore in the form of a lotion or ointment. Many of the substances that prove effective in the treatment of skin traumas do not naturally occur in a liquid or gelatinous state, and therefore must be combined with other substances so that they may be properly applied to the damaged area of the skin. Furthermore, many of the substances that are effective in promoting healing may cause pain or other discomfort when applied directly to an open wound. Therefore, people have attempted to find substances that may be combined with the active ingredients in order to alleviate the discomfort associated with topical treatment of an open sore or wound.

It has been found that a combination of cedar leaf oil, zinc oxide ointment, and calamine lotion with an ointment base such as anhydrous lanolin or petroleum jelly is effective in treating virtually all sores, wounds and skin traumas, including but not limited to burns, surgical incisions, skin ulcers and insect bites. So far as is known, though the prior art has sought to treat such skin traumas through the combination of various ingredients, no prior art combination has appreciated the surprising result achieved by combining cedar leaf oil, zinc oxide ointment, and calamine lotion with an ointment base such as anhydrous lanolin or petroleum jelly according to the invention hereinafter disclosed.

For example, the composition disclosed in U.S. Pat. No. 5,266,318 was used for treatment of irradiated skin, open sores, wounds and abrasions. The composition was comprised of an aloe vera gel extract, allantoin and lavender essential oil. The composition disclosed in U.S. Pat. No. 5,879,717 was comprised of a sugar, iodine and a glycol or water vehicle and was for the treatment of wounds and related conditions, and was specifically useful in veterinary medicine. The composition described in U.S. Pat. No. 5,980,875 was prepared by mixing honey with oil, a gelling agent, an emulsifier and other components, and was to be used for the treatment of Herpes, cold sores, burns, skin allergies and other wounds. In U.S. Pat. No. 6,099,866, beeswax was combined with oil and sometimes water to produce a composition for treatment of various burns and abrasions. None of these prior inventions has sought to combine cedar leaf oil with zinc oxide ointment or with calamine lotion and have therefore failed to achieve the benefits of such a combination.

SUMMARY OF INVENTION

In one embodiment of the present invention, a topical ointment for open wounds is described and comprises a solution of cedar leaf oil, zinc oxide ointment, calamine lotion and an ointment base. In the preferred embodiment the solution is approximately 10% cedar leaf oil by weight, approximately 10% zinc oxide ointment by weight, approximately 10% calamine lotion (medicated) by weight; and approximately 70% ointment base by weight. A suitable ointment base is 50% anhydrous USP lanolin with 50% pure petroleum jelly. Artificial food coloring may be added to tint the solution as desired. The ranges can be varied, with the calamine lotion varying from 2–10% by weight. Drier lesions respond better to lower ranges of calamine lotion, typically less than 5% for dry lesions and above 5% for oozing or moist lesions. A 2% calamine solution has been particularly useful in treating burns, Herpes Simplex 1, Herpes Simplex 2 and Herpes Zoster or Shingles.

Another variation of the solution can be used for the treatment of insect bites or stings. The anhydrous lanolin and petroleum jelly are to approximate 68% of the total solution by weight and 1–2% of hydrocortisone ointment is added as an additional component. For pure surgical healing and reduction of scarring from burns, lacerations or surgery, the cortisone is replaced with vitamin K.

The solution is thoroughly mixed by blending at room temperature. Once mixed, the solution is applied directly to the wound as a topical medication, and is applied repeatedly as it evaporates or wears. The treatment is continually applied of a period of days until the wound is healed. For severe wounds such as diabetic sores, as many as 30 to 40 days of application may be required, with excellent results having been achieved.

DESCRIPTION OF THE PREFERRED EMBODIMENT

Cedar leaf oil, otherwise known as thuja oil, may be produced through distillation of the leaves of the tree commonly known as the arbor vitae, which is also sometimes erroneously known as the "white cedar" —hence the inclusion of the word "cedar" in the name of the oil. In its pure form, cedar leaf oil may act as a neurotoxin, which means that it may cause damage to nerve tissues under certain circumstances. However, it has been found that if cedar leaf oil is appropriately diluted, according to the present invention, it may become an excellent topical analgesic, meaning that when applied directly to the skin or other tissue, it may relieve pain locally in the area where applied. Furthermore, in its diluted form, cedar leaf oil may act as a dehydriotic agent, meaning that it may be effective in removing moisture that is sometimes associated with open sores and wounds. Cedar leaf oil can be obtained from an ordinary pharmaceutical supply company such as the Professional Compounding Center of America, located in Houston, Tex.

Medicinal zinc oxide is a mixture of zinc peroxide, zinc carbonate, and zinc hydroxide, and is sometimes used topically in solution as a local anti-infectant and oxidant. It is also sometimes used as an astringent, which means that it may cause contraction of the tissues to which it is applied. Zinc oxide ointment is a preparation of zinc oxide and mineral oil, and is generally white in color. It is commonly used as an astringent and a protectant. Zinc oxide ointment can be obtained at many pharmacies and medical supply outlets throughout the United States.

Calamine consists of zinc oxide with a small proportion of ferric oxide. Calamine is normally a fine pink powder and is commonly used in the treatment of skin diseases. It has the qualities of being a mild astringent and protectant. Calamine lotion is a preparation of calamine with zinc oxide, glycerine, bentonite magma, and calcium hydroxide solution. Calamine lotion is commonly used as a protectant. Calamine lotion can be obtained at many pharmacies and medical supply outlets throughout the United States.

Lanolin is the purified fatlike substance from the wool of sheep, and generally appears as a yellowish-white mass. Anhydrous [USP] lanolin is lanolin that contains not more than 0.25% water, and is commonly used as an absorbent ointment base. An ointment base may be any substance suitable for use as a vehicle for medicinal substances intended for external application to the body. Anhydrous [USP] lanolin is produced by Paddock Labs, Inc.

Petroleum jelly, also known as petrolatum is a purified mixture of semisolid hydrocarbons obtained from petroleum and is often used as an ointment base, or by itself as a protective or to soothe the skin. Petroleum jelly can be obtained at nearly any pharmacy or large grocery store in the United States.

Hydrocortisone is a well known chemical that may be produced either by the human adrenal cortex, or synthetically. It is often used in the treatment of a wide array of ailments, including inflammations, allergies and arthritis. Hydrocortisone ointment is a preparation of hydrocortizone in an ointment base, and is generally used as an anti-inflammatory adrenocortical steroid. The brand name "Cortisone 10 With Aloe" is distributed by Pfizer, Inc.

Vitamin K refers generally to the group of fat soluble substances including phytonadione, menaquinone, and menadione. These substances may promote the clotting of the blood by increasing the synthesis of prothrombin by the liver. A standard injectable solution of vitamin K can be obtained from Robar Labs of Phoenix Ariz.

According to the present invention, cedar leaf oil, zinc oxide ointment and calamine lotion may be combined in varying proportions with various other substances to produce a solution which can be applied to an open sore or wound. The novel combination of the above described substances has been shown to accelerate healing of and reduce scarring from various skin sores and wounds. The present invention is not limited to any particular method of combining the constituents of the solution. It has been found that a sturdy kitchen type blender serves to adequately mix the ingredients into a homogeneous solution. Other mixing tools could be used, ranging from industrial food grade blending equipment to hand stirring with a whisk. Generally, for convenience, the ingredients are combined appropriately to form a 10 ounce unit, though wide variation is permitted.

The present invention contemplates the treatment of virtually any skin sore and is not limited to the treatment of any particular type of skin malady. As used herein, the words sore, wound or trauma refer broadly to any kind of irregularity, degradation or damage to the skin whether caused by injury, disease, or exposure to radiation, heat or harmful chemicals. The sores which the present invention may be useful in treating include but are not limited to diabetic ulcers, insect bites, surgical incisions, and burns. The vast majority of the sores that will be treated with the present invention will manifest themselves on the skin of a patient. However, some of the sores may occur on the patient's mucus membranes, such as the inner nostrils or lips. The word skin, as used herein, should therefore be understood to include all of the patient's tissues and membranes that can be accessed without surgical incisions or invasive medical procedures. These tissues may also be referred to as external tissues.

It is contemplated that the solution of the present invention will be applied directly, externally, to the sore which is the subject of treatment. In other words, the solution of the present invention is preferably not intended to be ingested or injected. Instead, it is preferably rubbed, applied or otherwise placed on the sore from the outside of the patient's body. Of course, the solution may be absorbed into the skin or other tissue being treated upon application of the solution to the sore. According to the invention, the solution may be rubbed into the wound or sore by hand or with a cotton swab or other similar sterile implement. The sore may then be covered with a bandage if desired, or may be left exposed to the air, depending upon the treatment regimen deemed appropriate. Alternatively, the solution may first be applied to a bandage and the bandage applied to the wound, thereby treating the wound and covering the wound at the same time.

It is desirable that the final solution be easy to apply and to handle. In some circumstances, the patient or medical practitioner may be applying the solution by hand or with a cotton swab. In such an instance it may be desirable that the solution be gelatinous or paste-like in consistency. On the other hand, the patient or medical practitioner may desire to pour the solution onto a bandage or piece of gauze first, and then apply the bandage or gauze to the wound. In that instance, it may be desirable that the final consistency of the solution be very thin or "runny." The present invention is not limited to any particular final solution density, and the medical personnel using the solution may desire that the ointment base be varied in order to achieve the desired consistency.

If desired, the solution may be administered on a periodic basis, or just once. It has been found that topical application, apply with a tongue depressor or similar device; three to four hours; bandages preferable open; cover with telpha; kept in place with paper tape. For best results it has been found that the wound must be continually covered with the solution over a period of days until the wound is fully healed.

The solution of the present invention generally comprises cedar leaf oil, zinc oxide ointment, calamine lotion and an ointment base. In one embodiment, the cedar leaf oil may comprise from about 5% to about 10% of the total weight of the solution, the zinc oxide may comprise from about 5% to about 10% of the total weight of the solution, and the calamine lotion may comprise from about 2% to about 10% of the total weight of the solution. An ointment base, such as petroleum jelly and USP lanolin may then be added to form the remainder of the weight of the solution. When the Wounds are dry, i.e. not producing or otherwise secreting fluids, the calamine lotion may comprise about 2% of weight of the solution. If the wounds are producing fluids, the calamine lotion may be increased to comprise about 5% of the solution. Preferably, where the wound is a burn or Herpes Simplex 1, Herpes Simplex 2, or Herpes Zoster, the calamine lotion comprises from about 2% to about 5% of the weight of the solution.

In a preferred embodiment, the cedar leaf oil comprises about 10% of the weight of the solution. It is also preferable that the zinc oxide ointment comprise about 10% of the weight of the solution. It is most preferable that the cedar leaf oil and the zinc oxide ointment be combined in substantially equal amounts, meaning that the weights of the two components do not vary from one another by more than 1%. It was found during the treatment of a diabetic foot ulcer, that excellent healing results were achieved by including both cedar leaf oil and zinc oxide ointment in substantially equal quantities of about 10% by weight of each. It was also found that using substantially equal amounts of cedar leaf oil, zinc oxide ointment and calamine lotion assisted in the healing process of diabetic foot ulcers.

Though the present invention contemplates the use of any ointment base, it has been found that anhydrous lanolin and petroleum jelly are particularly well suited for such purpose. In one embodiment the solution comprises about 39% by weight of petroleum jelly. In another embodiment, the solution comprises about 39% by weight of anhydrous USP lanolin. It has been found that using substantially equal amounts of petroleum jelly and anhydrous lanolin yields particularly good results in terms of ease of application, patient comfort and speed of healing.

Where the wounds or sores are especially prone to swelling, such as in the case of an insect bite or sting, it has been found that including hydrocortisone ointment speeds the healing process even further. Hydrocortisone ointment is also helpful in applications where the sores are not particularly prone to swelling. In one embodiment of the present invention, hydrocortisone ointment comprises from about 3% to about 5% by weight of the solution. Where hydrocortisone ointment is desirable, it is preferred that the amount of ointment base be reduced by a weight according to the amount of hydrocortisone ointment that is added. Alternatively, any of the other constituents may be reduced in proportion to accommodate the addition of the hydrocortisone ointment.

It has been found that in applications involving physical damage to the skin, such as burns, lacerations and surgical incisions, addition of vitamin K may be effective in promoting healing. In one embodiment, the vitamin K comprised from about 1% to about 2% of the total weight of the solution.

For commercial reasons, and to assist patients and medical practitioners in identifying the solution of the present invention, artificial food coloring may be added to give the solution a distinct and attractive appearance. It has been found that using red food coloring gives that solution a pink appearance which easy to recognize and is particularly appealing to medical practitioners and patients.

The foregoing disclosure and description of the invention are illustrative and explanatory thereof, and various changes in the components and quantities, as well as in the details of the described preparation and use may be made without departing from the spirit of the invention.

What is claimed is:

1. A solution for the topical treatment of skin sores comprising: cedar leaf oil comprising from about 5% to about 10% by weight; zinc oxide ointment comprising from about 5% to about 10% by weight; calamine lotion comprising from about 2% to about 10% by weight; and an ointment base.

2. The solution of claim 1 wherein the calamine lotion comprises from about 2% to about 5% by weight.

3. The solution of claim 1, wherein the calamine lotion comprises about 2% by weight.

4. The solution of claim 1, wherein the calamine lotion comprises about 5% by weight.

5. The solution of claim 1, wherein the cedar leaf oil comprises about 10% by weight.

6. The solution of claim 1, wherein the zinc oxide ointment comprises about 10% by weight.

7. The solution of claim 1, comprising substantially equal amounts of cedar leaf oil and zinc oxide ointment.

8. The solution of claim 1, comprising substantially equal amounts by weight of cedar leaf oil, zinc oxide ointment and calamine lotion.

9. The solution of claim 1, wherein the ointment base is selected from the list consisting of anhydrous lanolin, petroleum jelly.

10. The solution of claim 1, wherein the ointment base is comprised of about 39% by weight anhydrous lanolin and about 39% by weight of petroleum jelly.

11. The solution of claim 1, wherein the ointment base is comprised of substantially equal amounts by weight of anhydrous lanolin and petroleum jelly.

12. The solution of claim 1, further comprising from about 1% to about 2% by weight of hydrocortisone ointment.

13. The solution of claim 1, further comprising from about 1% to about 2% by weight of vitamin K.

14. The solution of claim 1, wherein the total weight of the solution is about 10 ounces.

15. The solution of claim 1, further comprising artificial food coloring.

16. A method of preparing a solution for treating skin sores comprising the step of:
   combining cedar leaf oil, zinc oxide ointment, and calamine lotion with an ointment base to form a treatment ointment; said cedar leaf oil comprising between about 5% and about 10% by weight of said solution.

17. The method of preparing the solution of claim 16, wherein the cedar leaf oil is combined to comprise about 10%, by weight of the treatment solution.

18. The method of preparing the solution of claim 16, wherein the zinc oxide ointment is combined to comprise from about 10% by weight of the treatment solution.

19. The method of preparing the solution of claim 16, wherein the calamine lotion is combined to comprise from about 2% to about 10% by weight of the treatment solution.

20. The method of preparing the solution of claim 16, wherein the calamine lotion is combined to comprise from about 2% to about 5% by weight of the treatment solution.

21. The method of preparing the solution of claim 16, wherein the calamine lotion is combined to comprise about 2% by weight of the treatment solution.

22. The method of preparing the solution of claim 16, wherein the calamine lotion is combined to comprise about 5% by weight of the treatment solution.

23. The method of preparing the solution of claim 16, wherein the zinc oxide ointment is combined to comprise about 10% by weight of the treatment solution.

24. The method of preparing the solution of claim 16, wherein the calamine is combined to comprise about 10% by weight of the treatment solution.

25. The method of preparing the solution of claim 16, wherein the cedar leaf oil and the zinc oxide ointment are combined in substantially equal amounts.

26. The method of preparing the solution of claim 16, wherein the ointment base is selected from the list consisting of anhydrous lanolin and petroleum jelly.

27. The method of preparing the solution of claim 16, further comprising the step of combining substantially equal amounts of anhydrous lanolin and petroleum jelly to form the ointment base.

28. The method of preparing the solution of claim 16, wherein the step of combining cedar leaf oil, zinc oxide ointment, and calamine lotion with an ointment base further includes combining hydrocortizone ointment to form the treatment solution.

29. The method of preparing the solution of claim 16, wherein the step of combining cedar leaf oil, zinc oxide ointment, and calamine lotion with an ointment base further includes combining vitamin K to form the treatment solution.

30. A method of treating skin sores comprising the step of:
applying a treatment solution to the skin sore, wherein the treatment solution comprises cedar leaf oil, zinc oxide ointment, calamine lotion and an ointment base; said cedar leaf oil comprising between about 5% and about 10% by weight of said solution.

31. The method of treating skin sores of claim 31, wherein the treatment solution is applied to a burn.

32. The method of treating skin sores of claim 31, wherein the treatment solution is applied to a diabetic skin ulcer.

33. The method of treating skin sores of claim 31, wherein the treatment solution is applied to a blister caused by Herpes Simplex 1.

34. The method of treating skin sores of claim 31, wherein the treatment solution is applied to a blister caused by Herpes Simplex 2.

35. The method of treating skin sores of claim 31, wherein the treatment solution is applied to a blister caused by Herpes Zoster.

36. The method of treating skin sores of claim 31, wherein the treatment solution is applied to an insect bite.

37. The method of treating skin sores of claim 31, wherein the treatment solution is applied to a surgical incision.

38. The method of treating skin sores of claim 31, wherein the treatment solution is applied to a laceration.

39. The method of treating skin sores of claim 31, further comprising the step of periodically re-applying the treatment solution.

40. The method of treating skin sores of claim 31, further comprising the step of covering the dermal tissue with a bandage.

41. The method of treating skin sores of claim 31, wherein the treatment solution is applied to a human patient.

* * * * *